United States Patent
Korzinov et al.

(10) Patent No.: US 11,246,531 B2
(45) Date of Patent: Feb. 15, 2022

(54) FATIGUE MEASUREMENT IN A SENSOR EQUIPPED GARMENT

(71) Applicant: Mad Apparel, Inc., Redwood City, CA (US)

(72) Inventors: Lev Korzinov, San Diego, CA (US); Ankit Gordhandas, Sunnyvale, CA (US); Christopher John Wiebe, Burlingame, CA (US)

(73) Assignee: Mad Apparel, Inc., Redwood City, CA (US)

(*) Notice: Subject to any disclaimer, the term of this patent is extended or adjusted under 35 U.S.C. 154(b) by 363 days.

(21) Appl. No.: 16/409,373

(22) Filed: May 10, 2019

(65) Prior Publication Data
US 2019/0343459 A1    Nov. 14, 2019

Related U.S. Application Data

(60) Provisional application No. 62/669,799, filed on May 10, 2018.

(51) Int. Cl.
*A61B 5/00* (2006.01)
*A63B 24/00* (2006.01)
(Continued)

(52) U.S. Cl.
CPC .......... *A61B 5/6804* (2013.01); *A61B 5/0004* (2013.01); *A61B 5/02405* (2013.01);
(Continued)

(58) Field of Classification Search
CPC ....... A61B 5/296; A61B 5/0006; A61B 5/726; A61B 71/0622; A61B 24/0062;
(Continued)

(56) References Cited

U.S. PATENT DOCUMENTS

| | | |
|---|---|---|
| 6,623,427 B2 | 9/2003 | Mandigo |
| 9,445,759 B1 | 9/2016 | Lamego et al. |

(Continued)

FOREIGN PATENT DOCUMENTS

| | | | | |
|---|---|---|---|---|
| WO | WO 91/011221 A1 | 8/1991 | | |
| WO | WO-2016110804 A1 * | 7/2016 | ........... | A61B 5/0002 |

(Continued)

OTHER PUBLICATIONS

International Search Report and Written Opinion, PCT Application No. PCT/US2016/067372, dated Apr. 12, 2017, 24 pages.
(Continued)

*Primary Examiner* — Yoshihisa Ishizuka
(74) *Attorney, Agent, or Firm* — Fenwick & West LLP

(57) ABSTRACT

An exercise feedback system determines muscle fatigue measurements using physiological data generated by a sensor-equipped athletic garment. The muscle fatigue measurement is determined by analyzing the frequency spread of the physiological data. The exercise feedback system may customize exercise programs, determine risks of injury, or generate biofeedback for presentation on graphical user interfaces using the muscle fatigue measurements. The exercise feedback system accesses pre-determined muscle fatigue measurement models that define criteria for the aforementioned features. For instance, if an athlete is becoming fatigued and exercising with improper form based on a muscle fatigue measurement, the exercise feedback system modifies the athlete's exercise program to help target and improve the athlete's weaknesses as well as to prevent injury.

21 Claims, 7 Drawing Sheets

(51) Int. Cl.
*A61B 5/024* (2006.01)
*A63B 71/06* (2006.01)
*A61B 5/296* (2021.01)
*A61B 5/316* (2021.01)

(52) U.S. Cl.
CPC .............. *A61B 5/296* (2021.01); *A61B 5/316* (2021.01); *A63B 24/0062* (2013.01); *A63B 71/0622* (2013.01); *A61B 2503/10* (2013.01); *A61B 2560/0223* (2013.01); *A61B 2562/046* (2013.01); *A63B 2220/836* (2013.01); *A63B 2230/08* (2013.01)

(58) Field of Classification Search
CPC ..... A61B 5/6804; A61B 5/7203; A61B 5/316; A61B 5/02405; A61B 5/389; A61B 5/0004; A61B 2562/046; A61B 2503/10; A61B 2560/0223; A61B 2230/08; A61B 2220/0836
See application file for complete search history.

(56) References Cited

U.S. PATENT DOCUMENTS

| | | |
|---|---|---|
| 9,720,515 B2 | 8/2017 | Wagner et al. |
| 10,065,074 B1 | 9/2018 | Hoang et al. |
| 10,357,688 B2 | 7/2019 | Wiebe et al. |
| 10,362,993 B2 | 7/2019 | Wiebe et al. |
| 2005/0107719 A1 | 5/2005 | Arad (Abbound) |
| 2005/0177059 A1 | 8/2005 | Koivumaa et al. |
| 2006/0136173 A1 | 6/2006 | Case et al. |
| 2007/0232453 A1 | 10/2007 | Hanoun |
| 2008/0262392 A1 | 10/2008 | Ananny et al. |
| 2009/0171233 A1 | 7/2009 | Lanfermann et al. |
| 2010/0268477 A1 | 10/2010 | Mueller et al. |
| 2010/0312508 A1 | 12/2010 | Mott et al. |
| 2012/0004696 A1 | 1/2012 | Sun et al. |
| 2012/0071732 A1 | 3/2012 | Grey et al. |
| 2012/0123232 A1* | 5/2012 | Najarian .............. A61B 5/0022 600/345 |
| 2012/0143093 A1 | 6/2012 | Stirling et al. |
| 2012/0271143 A1 | 10/2012 | Aragones et al. |
| 2013/0041590 A1 | 2/2013 | Burich et al. |
| 2013/0136301 A1 | 5/2013 | Abrahamsson et al. |
| 2014/0135593 A1 | 5/2014 | Jayalth et al. |
| 2014/0142459 A1 | 5/2014 | Jayalth et al. |
| 2014/0235965 A1 | 8/2014 | Tran |
| 2014/0318699 A1 | 10/2014 | Longinotti-Buitoni et al. |
| 2014/0378858 A1 | 12/2014 | Armitage et al. |
| 2015/0088284 A1 | 3/2015 | Hendricks et al. |
| 2015/0120016 A1 | 4/2015 | Houmanfar et al. |
| 2015/0148619 A1 | 5/2015 | Berg et al. |
| 2015/0220486 A1* | 8/2015 | Karakonstantis ..... G06F 17/148 708/205 |
| 2015/0230719 A1 | 8/2015 | Berg et al. |
| 2015/0272482 A1 | 10/2015 | Houmanfar et al. |
| 2015/0272483 A1 | 10/2015 | Etemad et al. |
| 2015/0272501 A1 | 10/2015 | MacEachern et al. |
| 2015/0282768 A1 | 10/2015 | Luna et al. |
| 2015/0309563 A1 | 10/2015 | Connor |
| 2015/0351690 A1 | 12/2015 | Toth et al. |
| 2015/0366504 A1 | 12/2015 | Connor |
| 2016/0038083 A1 | 2/2016 | Ding et al. |
| 2017/0071548 A1 | 3/2017 | Wiebe et al. |
| 2017/0173391 A1 | 6/2017 | Wiebe et al. |
| 2017/0296083 A1* | 10/2017 | Cardenas ............... A61B 5/389 |
| 2018/0133551 A1 | 5/2018 | Chang et al. |
| 2018/0140901 A1 | 5/2018 | Wiebe et al. |
| 2018/0140902 A1 | 5/2018 | Wiebe et al. |
| 2018/0160966 A1* | 6/2018 | Inan ..................... A61B 5/0295 |
| 2019/0029594 A1 | 1/2019 | Jiang et al. |
| 2019/0046107 A1 | 2/2019 | Jang et al. |
| 2019/0046839 A1 | 2/2019 | Jang et al. |
| 2019/0076699 A1 | 3/2019 | Wiebe et al. |
| 2019/0282856 A1 | 9/2019 | Wiebe et al. |
| 2019/0290181 A1 | 9/2019 | Mrvaljevic et al. |
| 2019/0343459 A1 | 11/2019 | Korzinov et al. |
| 2019/0344121 A1 | 11/2019 | Wells et al. |

FOREIGN PATENT DOCUMENTS

| | | | |
|---|---|---|---|
| WO | WO 2016/149751 A1 | 9/2016 | |
| WO | WO-2016178523 A1 * | 11/2016 | ............. A61B 5/112 |

OTHER PUBLICATIONS

International Search Report and Written Opinion, PCT Application No. PCT/US2018/046565, dated Dec. 7, 2018, 18 pages.

Tank, P., Muscles of the Lower Limb, Department of Neurobiology and Developmental Sciences, University of Arkansas for Medical Sciences, 2009, retrieved online from http://anatomy.uams.edu/muscles_lowerlimb.html on Oct. 30, 2020, 9 pages.

* cited by examiner

400

Receive physiological data from a garment worn by a user
410

Determine and remove noise from the physiological data
420

Determine a power spectrum from the physiological data
430

Determine a spectrum ratio using the power spectrum
440

Determine a fatigue measurement using the spectrum ratio
450

Provide the fatigue measurement for display
460

FATIGUE MEASUREMENT IN A SENSOR EQUIPPED GARMENT

CROSS REFERENCE TO RELATED APPLICATION

This application claims the benefit of U.S. Provisional Application 62/669,799, entitled "Measuring Fatigue in a Sensor-Equipped Athletic Garment," filed May 10, 2018, which is incorporated herein by reference in its entirety.

BACKGROUND

This description generally relates to sensor-equipped athletic garments, and specifically to determining muscle fatigue using physiological data from the sensors.

Sensors record a variety of information about the human body. For example, electrocardiograph (ECG) electrodes can measure electrical signals from the skin of a person that are used to determine the person's heart rate. In addition, electromyography (EMG) electrodes can measure electrical activity generated by a person's muscles. Heart rate and muscle activation information may be useful for evaluating the person's physiological condition, for instance, while exercising. It is difficult to provide comparable metrics between different muscle groups for a given athlete and between different athletes since the muscle response depends on muscle physiology and body composition, which may vary between muscles and between athletes. A system that generates inconsistent metrics of athletic performance provides a poor user experience, and the athletes may not be able to improve their athletic training with unreliable feedback on exercises.

SUMMARY

An exercise feedback system determines muscle fatigue measurements using physiological data generated by a sensor-equipped athletic garment. Muscle fatigue is characterized by a reduction in the force producing capacity of a muscle and can be measured using electromyography (EMG) signals. Muscle fatigue includes both peripheral fatigue due to changes in the muscle itself and central fatigue due to changes in the neural drive to the muscle. Surface EMG signals show signs of both peripheral and central fatigue through amplitude and frequency changes. Various embodiments described herein determine muscle fatigue measurements from electromyography (EMG) data. The exercise feedback system determines the muscle fatigue measurements from frequency or power spectrum changes because the frequency or power spectrum changes are more stable compared to amplitude changes. EMG amplitude is strongly influenced by the intensity of activation of a muscle. However, frequency changes are more influenced by muscle fatigue than changes in intensity of activation and can therefore provide more stable representation of fatigue changes of a muscle. The exercise feedback system removes artifacts such as a baseline shift from raw EMG signals. In addition, the exercise feedback system compensates for interferences caused by dynamic exercises.

The exercise feedback system may customize exercise programs, determine risks of injury, or generate biofeedback for presentation on graphical user interfaces using the muscle fatigue measurements. In an embodiment, the exercise feedback system accesses pre-determined muscle fatigue measurement models that define criteria for the aforementioned features. For instance, responsive to determining that an athlete is becoming fatigued, the exercise feedback system modifies the athlete's exercise program to help target and improve the athlete's weaknesses. Additionally, if the exercise feedback system determines that the athlete is susceptible to injury, the exercise feedback system notifies the athlete of the risk of injury.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

I. System Overview

Figure 1:
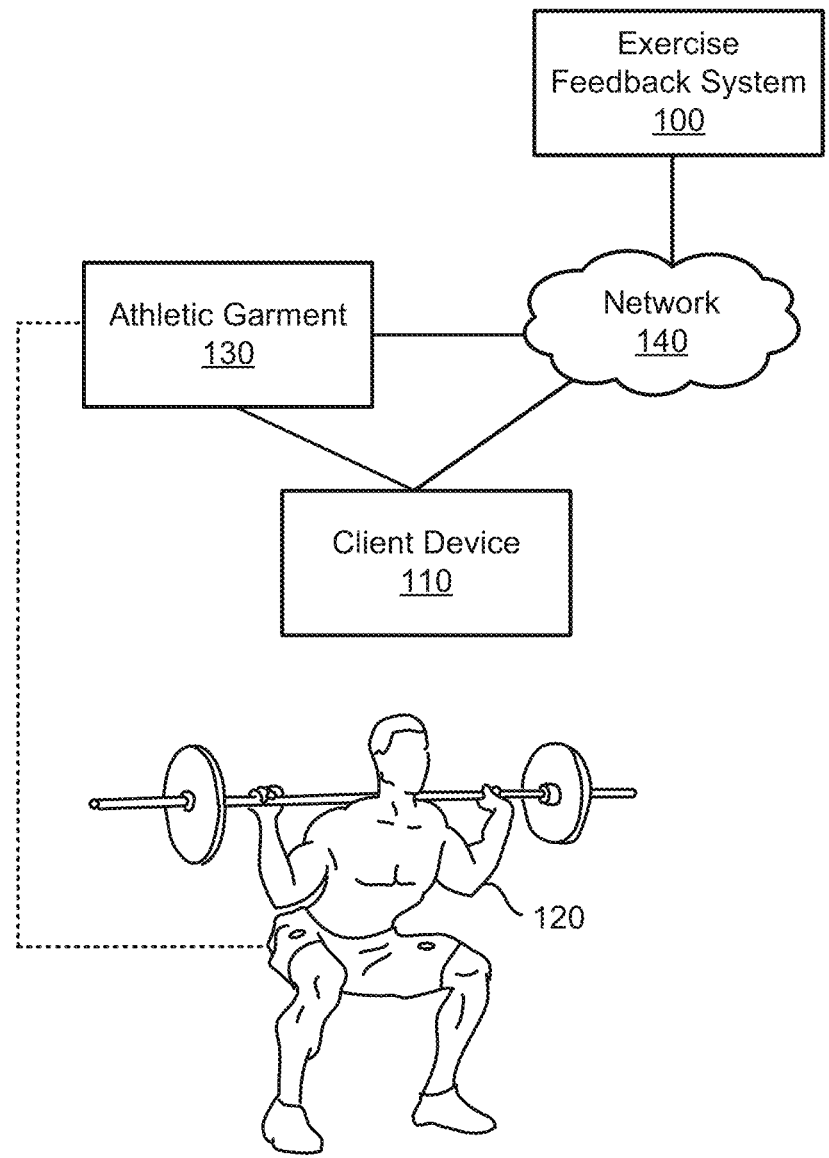
FIG. 1 is a diagram of a system environment for determining muscle fatigue measurements according to one embodiment.

FIG. 1 is a diagram of a system environment for monitoring exercise data according to one embodiment. The system environment includes an exercise feedback system 100, client device 110, and athletic garment 130 communicatively coupled together via a network 140. Users 120 of the exercise feedback system 100 are also referred to herein as "athletes." In other embodiments, different and/or additional entities can be included in the system architecture.

The client device 110 is a computing device capable of receiving user input as well as transmitting and/or receiving data via the network 140. A client device is a device having computer functionality, such as a smartphone, personal digital assistant (PDA), a mobile telephone, tablet, laptop computer, desktop computer, a wearable computer (such as a smart watch, wrist band, arm band, chest band, or the like), or another suitable device. In one embodiment, a client device executes an application allowing a user of the client device to interact with the exercise feedback system 100. For example, a client device executes a browser application to enable interaction between the client device and the exercise feedback system 100 via the network 140. In another embodiment, a client device 110 interacts with the exercise feedback system 100 through an application programming interface (API) running on a native operating system of the client device, such as IOS® or ANDROID™.

An athlete 120 wears the athletic garment 130 (further described below with reference to FIG. 2) while performing exercises. The athletic garment 130 records physiological data, e.g., muscle activation data or heart rate data, of the athlete. Based on the physiological data, the exercise feedback system 100 determines muscle fatigue measurements or biofeedback customized for the athlete. The muscle fatigue measurements may correspond to any muscle, portion of a muscle, or set of muscles of the athlete. For example, the athlete's biceps may include a left and right biceps muscle, and the biceps may be part of a group of upper body muscles. As described herein, a muscle includes soft tissue for the purpose of producing force or motion of the human body, and may be a slow twitch or fast twitch type of muscle. Further, a coach of the athlete can view the biofeedback on a client device 110 and provide additional feedback for the athlete. In some embodiments, the exercise feedback system 100 can communicate feedback using audio output or haptic feedback of the client device 110.

II. Example Athletic Garment

Figure 2:
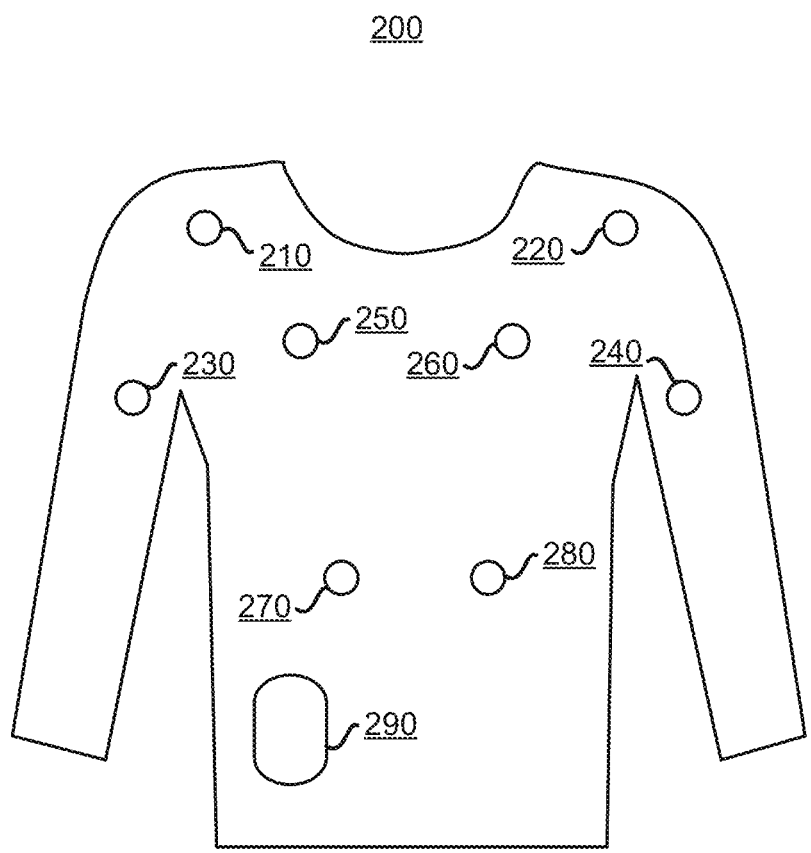
FIG. 2 is a diagram of a sensor-equipped athletic garment according to one embodiment.

FIG. 2 is a diagram of a sensor-equipped athletic garment 200 according to one embodiment. The athletic garment 200 includes sensors that contact the skin of an athlete wearing the athletic garment 200. For example, the sensors can be electrodes that measure electromyography (EMG) signals (electrical signals caused by muscle cells) also referred to as muscle activation data or muscle activation levels, electrocardiograph (ECG) signals (electrical signals caused by depolarization of the user's heart muscle in particular) also referred to as heart rate data, electrical signals modified by the tissue of the user (also referred to as bioimpedance data), electroencephalograph (EEG) signals, magnetoencephalograph (MEG) signals, among other types of signals associated with physiological data. The sensors may also include other types of sensors such as accelerometers and gyroscopes (which generate motion data based on the athlete's movement), temperature sensors, pressure sensors, humidity sensors, geographical location sensors, etc. The sensors generate physiological data of the athlete based on the measured signals. The sensors are communicatively coupled to a processing unit 290. The processing unit 290 can aggregate and analyze the physiological data from the sensors. The processing unit 290 can also provide the physiological data to the client device 110 or exercise feedback system 100 via the network 140.

In the embodiment shown in FIG. 2, the athletic garment 200 includes eight sensors that record muscle activation data from the athlete's muscles nearby each sensor. In particular, sensors 210 and 220 located on the right and left shoulder of the athletic garment 200 can record muscle activation data of the athlete's deltoid muscles. Sensors 230 and 240 located on the right and left sleeves of the athletic garment 200 can record muscle activation data of the athlete's triceps and/or bicep muscles. Sensors 250 and 260 located on the right and left chest of the athletic garment 200 can record muscle activation data of the athlete's pectoral muscles. Sensors 270 and 280 located on the right and left abdomen of the athletic garment 200 can record muscle activation data of the athlete's abdominal and oblique muscles. Though the athletic garment 200 shown in FIG. 2 includes eight sensors and the processing unit 290, in other embodiments, the athletic garment 200 can include any number of sensors or other types of components or electronics at any location or configuration within the athletic garment 200.

It should be noted that while the athletic garment 200 shown in FIG. 2 is a long sleeve shirt, the principles described herein apply equally to any garment, including but not limited to a short sleeved shirt, a tank top, pants, shorts (e.g., the athletic garment 130 shown in FIG. 1), or any other suitable garment. In embodiments where the athletic garment is a pant or shorts, sensors of the athletic garment can record muscle activation data from muscles on an athlete's lower body, e.g., inner and outer quadriceps (also referred to as "quads"), gluteus maximus (also referred to as "glutes"), hamstrings, calves, and the like.

III. Example Exercise Feedback System

Figure 3:
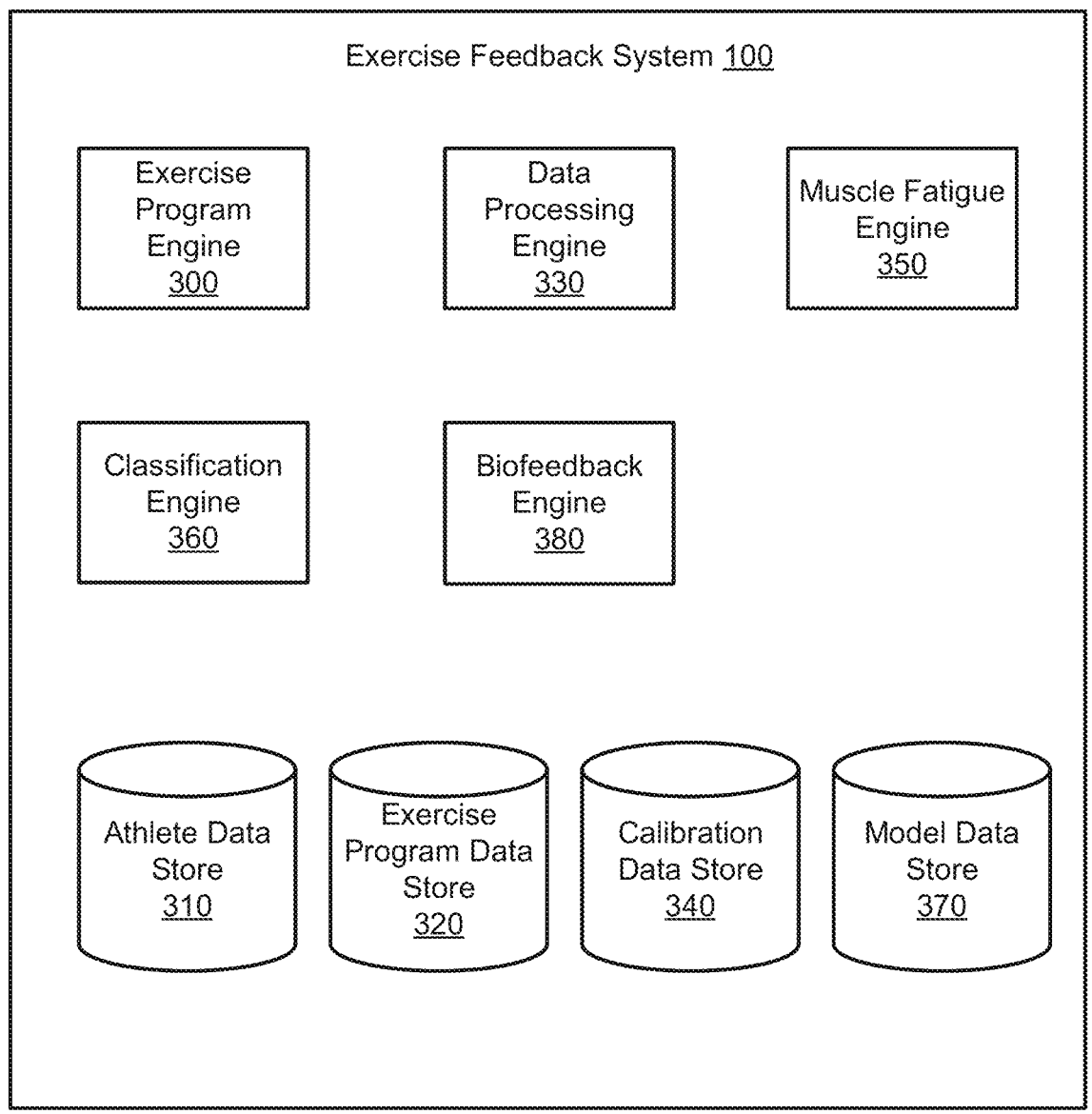
FIG. 3 is a block diagram of an exercise feedback system according to one embodiment.

FIG. 3 is a block diagram of the exercise feedback system 100 according to one embodiment. The exercise feedback system 100 includes an exercise program engine 300, an athlete data store 310, an exercise program data store 320, a data processing engine 330, a calibration data store 340, a muscle fatigue engine 350, a classification engine 360, a model data store 370, and a biofeedback engine 380. In other embodiments, the exercise feedback system 100 may include additional, fewer, or different components for various applications, which are not shown for purposes of clarity.

The exercise program engine 300 manages exercise programs for athletes of the exercise feedback system 100. In some embodiments, an athlete joins the exercise feedback system 100 by completing an onboarding process during which the exercise program engine 300 receives user information and physiological data associated with the athlete and stores the user information and physiological data in the athlete data store 310. User information includes, for example, demographic data (e.g., age, gender, ethnicity, etc.), geographic data, exercise related data (e.g., sports played, a specific position for sport, or sports team information), or physiological data (e.g., height or weight). Physiological data may include data generated by the sensors of athletic garment 200 while the user performs prescribed onboarding baseline exercises. The sensor data generated during the onboarding baseline may be used to set calibration parameters or reference levels for each muscle group such that subsequent metrics for that muscle can be reported as a relative percentage from the onboarding baseline. Calibration parameters are stored in the calibration data store 340. Exercise programs may include various exercises or other athletic related activities (e.g., diet or medical health data), and the exercise program engine 300 may customize the types and number of exercises for a given athlete based on user information retrieved from the athlete data store 310.

In some embodiments, heart rate variability can be used to determine a beginning or pre-workout fatigue measurement for a user. In these embodiments, the initial heart rate variability of the user can be used to calibrate or set a baseline fatigue level for the athlete. Increases to the fatigue level of the athlete during workout calculated based on the EMG signal as described herein can be used to show the relative increase of fatigue to the user.

The exercise program engine 300 may generate or update exercise programs based on information from the exercise program data store 320, which includes a database of exercises and other types of athletic training information or guidelines and/or fatigue-associated measurements for a user, as described in more detail below. An exercise program may include exercise sets (also referred to as a "set"), where a set includes a number of repetitions of an exercise to be performed in sequence. As an example use case, the exercise program engine 300 determines that a given athlete is a basketball player aiming to increase their vertical jump height. Thus, the exercise program engine 300 updates an exercise program for the given athlete that includes exercises for developing lower body strength such as squats and calf raises. Moreover, the exercise program engine 300 may determine a suitable weight for the exercises and update the weight over time based on the athlete's performance, e.g., responsive to determining that the athlete has increased strength, the exercise program engine 300 increases the amount of weight to lift per repetition of an exercise. By personalizing exercise programs, the exercise program engine 300 determines strengths and weaknesses specific to an athlete, which helps improve the effectiveness of the athlete's training.

The data processing engine 330 conditions physiological data generated by sensors of an athletic garment (e.g., athletic garment 200 shown in FIG. 2) for muscle fatigue measurements determination. The data processing engine 330 can receive the physiological data from the client device 110 or the processing unit 290 of the athletic garment 200. In some embodiments, the data processing engine 330 pre-processes the physiological data by performing noise filtering techniques.

The data processing engine 330 removes artifacts from the physiological data. As described herein, artifacts refer to noise signals that interfere with a power spectrum of the portion of the physiological data that measures the muscle fatigue. Artifacts may be periodic or nonperiodic and may result from different causes such as loose sensor contacts, movement between the sensor contact and athlete's body and movement or impact of the athlete's body experienced during exercise. The artifacts have a greater magnitude when the contact between the sensor and athlete's body is less stable or at a higher impedance. EMG signals can include many artifacts that can both corrupt the useful portions of EMG signals and unpredictably alter the power spectrum of the EMG signals. Removing artifacts in the EMG signals efficiently can allow subtle power spectrum changes to be detected while increasing the portions of the EMG signals that are preserved.

A baseline shift is one type of artifact. The baseline shift occurs as a result of a baseline movement change (e.g., from sitting to standing, electrode movement). The data processing engine 330 determines a baseline shift and removes the baseline shift from the physiological data. For example, the data processing engine 330 applies a Wavelet-based trend estimator to the EMG signals to determine the baseline shift. The EMG signals are transformed using a continuous wavelet transform and the higher order wavelets are removed. The baseline shift signal is determined by applying an inverse wavelet transform to only lower order coefficients. In some embodiments, the wavelet transform applied to the EMG signals is the 7-th order Symmlets wavelet transform (Sym7), and the cutoff threshold is 0.017. The baseline shift signal is then filtered out from the original EMG signal to reduce the baseline noise.

The data processing engine 330 may apply one or more of a low pass filter, a high pass filter, a band pass filter, and a band stop filter to remove artifacts. The low pass filter can function to remove higher frequency noise and the high pass filter can function to remove lower frequency noise (e.g., due to waist movement/pressure artifacts). The band pass filter can function to remove frequency noise beyond a particular frequency band. The band stop filter is used to attenuate signals of a particular frequency band and may be used to filter out the mains hum. However, different combinations of filters can be used to process different datasets. Additionally, the data processing engine 330 can perform other suitable condition processes such as smoothing, clipping, deconvolving, detrending/offsetting, standardizing, resampling, hard-binding, predicting, windowing, and the like. In one embodiment, the data processing engine 330 applies a band pass filter that outputs signals of which the frequency is in the range of 30 Hz and 300 Hz.

Additionally, physiological data generated by the sensors may vary due to athlete-to-athlete differences in physiological traits, sensor contact quality, among other factors. For instance, thicker hair on the athlete's skin or skin dryness may result in poor sensor contact quality, and thus reduce the amplitude of physiological data generated by the sensors and increase the amplitude of measured noise. As another example, skin oiliness or sweat may improve sensor contact quality, and thus increase the amplitude of physiological data generated by the sensors and reduce the amplitude of measured noise. The data processing engine 330 may determine a quality of physical contact between a sensor and the athlete's skin based on a measure of impedance between the sensor and athlete's skin, which is generated by another sensor or the same sensor. In some embodiments, the amplitude of physiological data generated by a sensor and the signal to noise ratio is inversely proportional to the impedance between the sensor and the skin of the athlete.

The data processing engine 330 normalizes physiological data between different types of muscles and different athletes to account for the above described sources of physiological data variation. The physiological data may vary based on parameters associated with the athlete wearing the athletic garment, e.g., differences in the physiology between multiple types of muscles influences the physiological data representing contraction of the muscles. For instance, the glutes and quads differ in the number of muscle fibers, fiber size, fiber type distribution (e.g., slow twitch or fast twitch), and thickness of adipose tissue between the muscle tissue and skin surface. The amplitude of physiological data (e.g., muscle activation level) may be proportional to the muscle fiber size and/or inversely proportional to the amount of fat between the muscle and the portion of skin.

Using normalized physiological data, the exercise feedback system 100 may provide biofeedback for a given type of muscle relative to other types of muscles. For example, the exercise feedback system 100 may provide a graphical user interface including a comparison of muscle fatigue measurements for multiple lower body muscles. Further, the data processing engine 330 may perform normalization using calibration parameters retrieved from the calibration data store 340. As an example, the glutes and quads have different calibration parameters, which are used by the data processing engine 330 to adjust raw amplitude values of the physiological data received for the two types of muscles. The data processing engine 330 may normalize physiological data by scaling the physiological data for a muscle corresponding to one of the sensors of an athletic garment 200 by a calibration parameter. In some embodiments, the data processing engine 330 generates a pre-processed EMG signal of the physiological data before normalization. For instance, the data processing engine 330 determines a power representation of the EMG signal by using averaging, a linear envelope, rolling root mean square or any other suitable technique to generate a pre-processed EMG signal. Additional filtering may be applied to the pre-processed signal to further filter and reduce potential noise sources. In an embodiment, the amplitude of the pre-processed EMG signal represents the power of contraction at a point in time, and the data processing engine 330 can determine the relative level of contraction by normalizing the pre-processed signal using the calibration parameters. As described below, normalization can also be attributed to determination of ratios of different frequency components of a signal (e.g., in the frequency domain).

Figure 5:
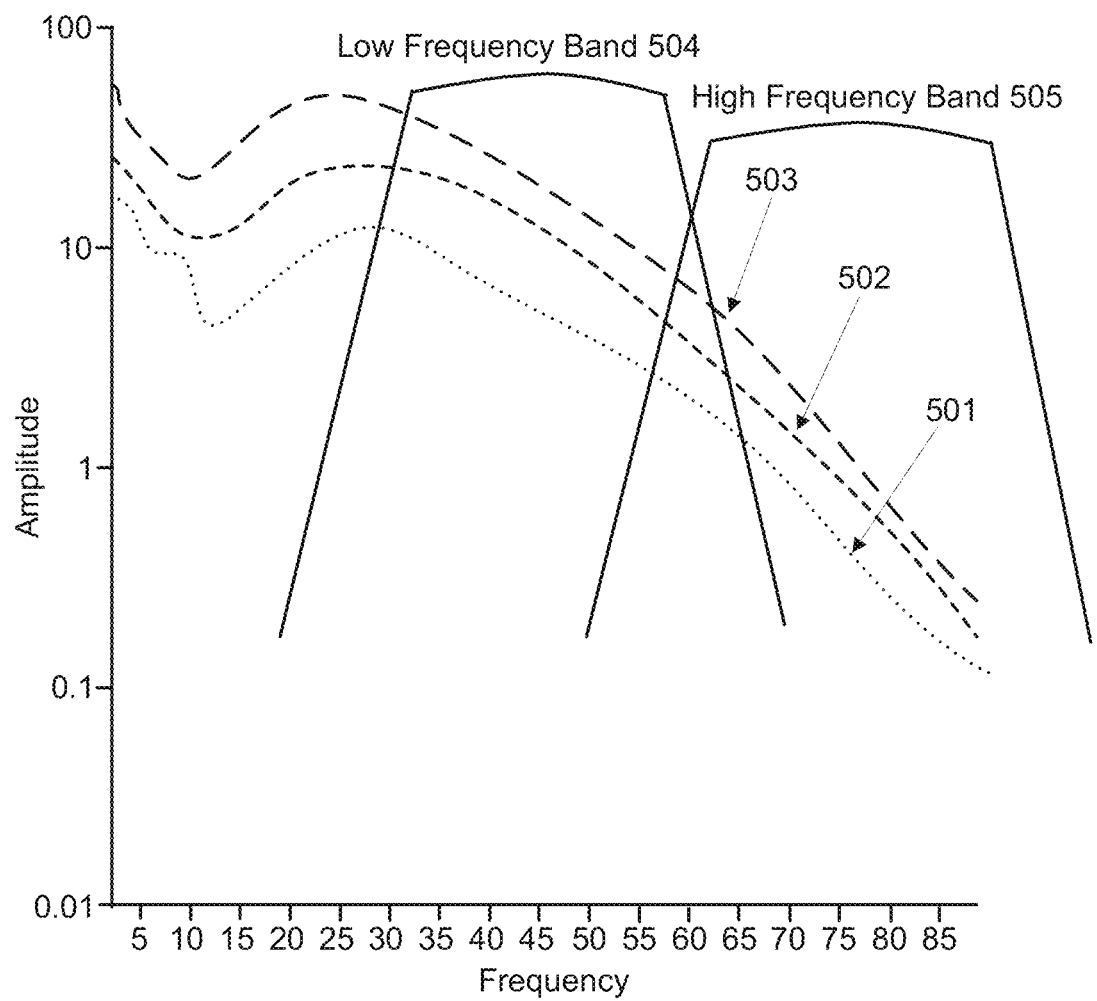
FIG. 5 is a diagram illustrating a power spectrum of an EMG signal according to one embodiment.

The muscle fatigue engine 350 determines a muscle fatigue measurement for a muscle. The muscle fatigue measurement is determined by using conditioned signals output from the data processing engine 330. In various embodiments, the muscle fatigue engine 350 determines a spectrum ratio of a first frequency band to a second frequency band of the conditioned signals. The spectrum ratio of the first frequency band to the second frequency band is a ratio between power of signal components in the first frequency band to power of signal components in the second frequency band. In one embodiment, the first frequency band is 30 to 60 Hz and the second frequency band is 60 to 150 Hz. If a particular muscle is closer to the fatigue state, the biggest change in spectrum power in the EMG signal is in the 30 to 60 Hz band. For example, as illustrated in FIG. 5, the change in power for signals in the low frequency band 504 is much greater than the change in power for signals in the high frequency band 505. Curves 501, 502, 503 represent the EMG signal captured from the quad muscle during an isometric hold at 5:00:00 pm, 5:00:10 pm, 5:00:20 pm. As a muscle fatigues, the frequency spectra of the EMG signal shifts to lower frequencies. As illustrated, the spread in the low frequency band 504 is much larger than the spread in the high frequency band 505, because the low frequency power increased more compared to high frequency. The ratio of low to high frequency therefore increases as the muscle fatigues. In other embodiments, the system can use other numbers of frequency bands (e.g., a low, medium, and high frequency band, more than 3 frequency bands, less than two frequency bands, etc.), other ranges of frequency bands, harmonics of frequency bands, frequency bands determined from other windows of data having other associated durations (e.g., less than 10 second windows, more than 10 second windows), etc.

The muscle fatigue engine 350 determines a power spectrum of the conditioned signal x(t). That is, the muscle fatigue engine 350 determines the distribution of power into frequency components of the conditioned signal x(t). In some embodiments, the muscle fatigue engine 350 determines the power spectrum ratio by using fast Fourier transform (FFT) or other signal processing techniques such as Welch method, Bartlett method. For example, the muscle fatigue engine 350 calculates the spectrum ration R by comparing signals in the high frequency band (e.g., 60-150 Hz) to signals in the low frequency band (e.g., 30-60 Hz) by applying FFT over a moving time window. In various embodiments, the spectrum is calculated over a moving time window (e.g., 10 seconds.)

In some embodiments, the muscle fatigue engine 350 applies a low frequency filter (e.g., 30-60 Hz) and a high frequency filter (e.g., 60-150 Hz) to obtain the signals in the low and high frequency bands. The muscle fatigue engine 350 then calculates the spectrum ratio R according to Equation (1):

$$R = A1(t)/A2(t) \quad (1),$$

where A1(t) and A2(t) represent the envelope of the low frequency (e.g., 30-60 Hz) and high frequency (e.g., 60-150 Hz) portions of the signal, respectively. The fatigue measurement may be interfered by a dynamic interference caused by repetitive movements. To substantially minimize the effect of these repetitive movements in measuring fatigue, the muscle fatigue engine 350 determines and removes dynamic interference from the fatigue measurement. The muscle fatigue engine 350 determines the dynamic interference by using the envelope H(x(t)) of the conditioned signal x(t). The muscle fatigue engine 350 applies a linear operator (e.g., Hilbert transform) to the conditioned signal x(t) to calculate the envelope H(x(t)) of the conditioned signal x(t). The muscle fatigue engine 350 determines the envelope of the conditioned signal x(t) using the envelope H(x(t)) according to Equation (3):

$$A(t) = |x(t)| + |H(x(t))| \quad (3).$$

The muscle fatigue engine 350 may calculate a series of simple moving averages SMA of the amplitudes A(t) to represent the envelope of signal x(t) Each simple average is calculated for a time interval. In some embodiments, the time interval is 5 seconds. In other embodiments, this time interval can be longer or shorter. The fatigue measurement calculates the dynamic interference according to Equation (1) or (2). The muscle fatigue engine 350 removes the dynamic interference from the spectrum ratio determined by using the conditioned signal x(t).

In an embodiment, the muscle fatigue engine 350 determines a start and stop time bound over which the muscle fatigue measurement is to be calculated. The start and stop time bound may indicate the start and end of a set of repetition. The muscle fatigue engine 350 may determine the start and stop time bound by examining the signal activity (e.g., by retrieving outputs of other sensors of the garment and/or associated with the user, such as accelerometers, gyroscopes, activity sensors, etc.). In one example, the muscle fatigue engine 350 compares the amplitudes of the conditioned signal x(t) to identify a pattern of the conditioned signal x(t) thereby to identify active regions and inactive regions. The muscle fatigue engine 350 determines active regions are time intervals during which the signals have substantially the same or similar curvature. For example, a change in amplitudes can be used to determine the curvature. During inactive regions, there is low signal activity and the calculation of muscle fatigue measurement is likely to be inaccurate and unstable. This also improves the system performance (e.g., determining a more accurate measurement of the muscle fatigue) as well as reduces the power consumption because the muscle fatigue engine 350 avoids calculating the muscle fatigue during the resting periods when the athlete is not performing the exercises (e.g., while resting between sets of exercises). The muscle fatigue engine 350 discards the physiological data generated by the sensors during inactive regions.

Figure 6:
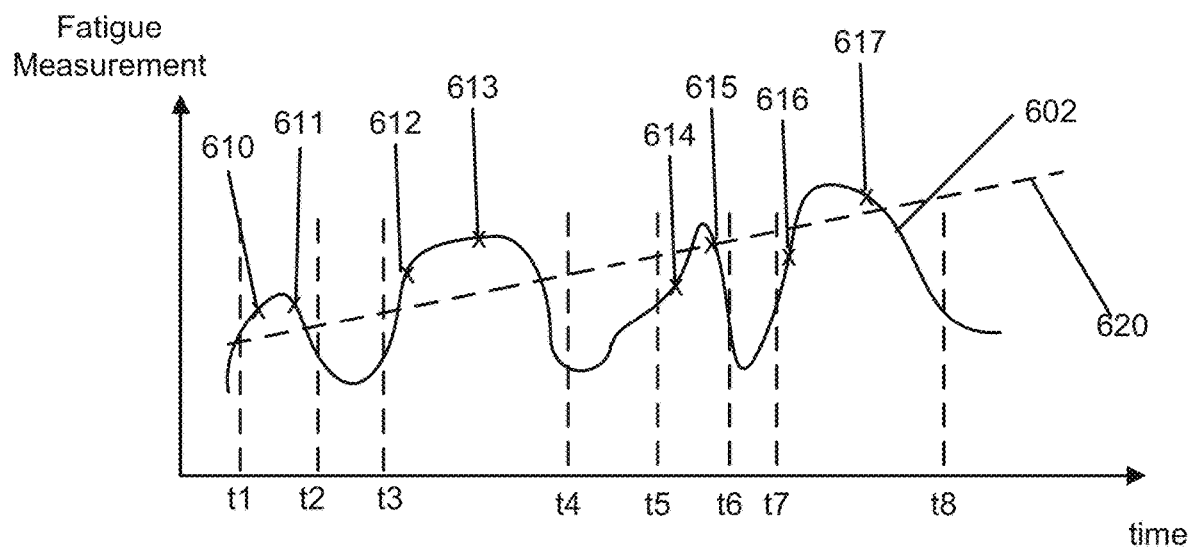
FIG. 6 is a diagram illustrating an example of a muscle fatigue engine determining the muscle fatigue measurements only during active regions according to one embodiment.

FIG. 6 illustrates one example of the muscle fatigue engine 350 determining the muscle fatigue measurements only during active regions. The muscle fatigue engine 350 determines that the time intervals t1-t2, t3-t4, t5-t6, t7-t8 are active regions. As illustrated, during the active regions, the muscle fatigue curve 602 reaches its local peaks indicating that the muscle fatigues during an exercise. During the inactive regions, the muscle fatigue curve 602 reaches its local minima indicating that the muscle recovers during a break. The muscle fatigue engine 350 calculates the fatigue measurements only during the active regions. The values 610-617 are example fatigue measurements that the muscle fatigue engine 350 determines. From the example values 610-617 an example overall fatigue progression can be derived. Taking fatigue measurements only during active periods provides a more accurate representation of fatigue progression during the workout.

In some embodiments, the muscle fatigue engine 350 accumulates normalized physiological data based on classifications determined by the classification engine 360. As an example, the classification engine 360 classifies normalized physiological data by determining a period of time during which an athlete actively performed an exercise or periods of time during which the athlete did not actively perform the exercise. The classification engine 360 can determine these periods of time without requiring manual input from the athlete. For instance, the classification engine 360 uses physiological data generated by the EMG sensors and motion data received from motion sensors of the athletic garment to determine whether the athlete is actively training, performing exercises, or performing a particular type of exercise. Based on the type of classification, the muscle fatigue engine 350 may perform active segmentation of sensor data received from the athletic garment, e.g., to provide exercise metrics and biofeedback. Similar to the time bound feature described above, the muscle fatigue engine 350 may improve the accuracy of muscle fatigue measurements by accumulating normalized physiological data received (or generated) during the active periods of time and not the inactive periods of time. In addition to resting between sets, an athlete may also briefly rest between repetitions or otherwise temporarily interrupt the exercise, e.g., to adjust the athletic garment. Classifying the active and inactive periods of time helps the muscle fatigue engine 350 account for these discrepancies in the physiological data.

In some embodiments, the classification engine 360 determines active or inactive periods of time for a given muscle or type of exercise. As an example, while an athlete is performing squat exercises, the classification engine 360 classifies the received sensor data to differentiate between physiological data for upper body muscles and lower body muscles. Since squat exercises are intended to train the lower body muscles, the classification engine 360 may determine active periods of time when the received physiological data for the lower body muscles has an amplitude or accumulated muscle fatigue greater than a threshold value. On the other hand, the classification engine 360 may process received physiological data for the upper body muscles when the athlete is performing exercises such as pullups, overhead lifts, pushups, or curls. In some embodiments, the classification engine 360 disregards physiological data—for determining muscle fatigue measurements of a particular muscle—generated during a given exercise responsive to determining that the given exercise is not directed to training that particular muscle. For instance, physiological data of the glutes and quads generated while the athlete is performing certain upper body exercises may not be normalized or accumulated for determining muscle fatigue measurements of the lower body muscles.

The classification engine 360 may also classify normalized physiological data based on quality of physical contact between a sensor and the athlete's skin. In particular, responsive to determining that the quality of physical contact during a period of time is less than a threshold quality (e.g., indicative of poor contact quality), the muscle fatigue engine 350 may exclude or modify the physiological data received during the period of time for determining muscle fatigue measurement. Other types of classification include, e.g., determining whether the received physiological data corresponds to a low, medium, or high intensity level of exercise; aerobic or anaerobic exercise; or a power, strength, endurance, speed, or hypertrophy type of exercise.

In some embodiments, the muscle fatigue engine 350 modifies or interprets physiological data received from a sensor over periods of poor contact quality, as classified by the classification engine 360. For example, if the contact quality is intermittently poor over short periods, the muscle fatigue engine 350 interprets physiological data during these short periods using sensor data received during other periods of good contact quality as boundary conditions for linear or polynomial curve fitting. Additionally, physiological data corresponding to sensors with poor contact quality (e.g., less than a given threshold) may be modified or interpreted by the muscle fatigue engine 350 using data from other sensors with good contact quality (e.g., equal to or greater than the given threshold). For example, when determining a fatigue measurement for the right hamstring muscle during a period of poor contact quality, the muscle fatigue engine 350 may use alternate physiological data corresponding to the left hamstring muscle, after determining that the alternate physiological data has good contact quality. Additionally, the muscle fatigue engine 350 may combine physiological data from multiple sensors to determine an approximate data set during a period of poor contact quality.

The muscle fatigue engine 350 may determine muscle fatigue measurements for a group of muscles. In addition, an athlete's general fatigue level can be computed based on these measurements. For instance, the various fatigue measurements for an athlete can be averaged, weighted and then averaged, or otherwise combined to produce a general fatigue measurement. In some embodiments, only the fatigue measurement corresponding to muscle groups used by the user during a particular workout may be combined to determine the user's general fatigue measurement. For example, if, during the course of a particular workout, a user receives a fatigue score of 60 for biceps, 70 for shoulders, and 92 for back, and if these muscle groups are the primary muscle groups exercised by the user during the particular workout, then an average fatigue score of 74 can be computed for the user for the workout. In other embodiments, a fatigue measurement for each of a set of muscle groups is determined and averaged, regardless of whether the user has exercised the muscle group during the workout. The muscle fatigue engine may assign a higher weight to fatigue measurements associated with muscle groups more correlative to general fatigue as compared to those associated with muscle groups less correlative to general fatigue. Fatigue in particular muscle groups can be more correlative to general fatigue measurements than others. For instance, back and core muscles may be more correlative to general fatigue than bicep muscle.

The muscle fatigue engine 350 may compute fatigue measurements repeatedly or continually over the course of a workout. For instance, as a user performs sets of exercises corresponding to a particular workout, a fatigue measurement can be computed for each set of exercises performed by the user. These computed fatigue measurements can be displayed on a graph indicating an increase in fatigue over the course of the workout. In some embodiments, such temporal displays of fatigue measurements can be displayed in conjunction with a "maximum fatigue" for a user. As used herein, "maximum fatigue" can refer to a threshold level of fatigue at which a user is no longer effectively able to use a particular muscle group to perform a particular exercise. The maximum fatigue for a user can vary based on the type of exercise being performed by the user, the muscle group being exercised, demographic data associated with the user (e.g., the user's weight, age, etc.), the maximum fatigue for users demographically similar to the user, historical fatigue data and maximum fatigue thresholds determined for the user, and the like. In some embodiments, the maximum fatigue can refer to a threshold at which a user is at an increased risk of injury or at which the benefits of the training have diminished. A trajectory of the athlete's fatigue can be compared to this maximum threshold to give the athlete an estimate of when the fatigue accumulation could become too high, potentially putting the athlete at risk of injury or decreasing the benefits of training. Additionally the maximum can correspond to a numerical upper bound for the fatigue measure, e.g. 100 as a muscle fatigue limit.)

The muscle fatigue engine 350 provides the muscle fatigue measurements for display. The muscle fatigue engine 350 may generate one or more user interfaces for presenting the muscle fatigue measurements or provide the muscle fatigue measurement to the client device for display. In some embodiments, the muscle fatigue engine 350 displays a fatigue measurement as a numerical value from 0 (not fatigued) to 100 (a muscle or movement capacity limit). Alternatively, the fatigue measurement can be displayed in a suitable form. In some embodiments, the muscle fatigue engine 350 displays the fatigue measurements on a muscle group-by-muscle group basis. For instance, a first fatigue measurement for a user's hamstrings can be displayed (for instance, on an overlay of a human body), a second fatigue measurement for a user's quads can be displayed, and a third fatigue measurement for a user's glutes can be displayed.

In some embodiments, the muscle fatigue engine 350 calculates a fatigue measurement for a first user, and display the result in conjunction with fatigue measurements computed for demographically similar users. For instance, the muscle fatigue engine 350 presents to the first user that the computed fatigue score of 80 in conjunction with an average fatigue score of 60 for users of a similar size/weight/height/age performing the same workout. Beneficially, such a system enables a user to evaluate the user's performance and athleticism relative to similar other users, enables the user to establish performance goals related to fatigue measures, and the like. In some embodiments, the muscle fatigue engine 350 provides an overall fatigue measurement of the athlete both during training and during recovery periods between training sessions using a combination of HRV and the EMG signal as described above.

The muscle fatigue engine 350 may present fatigue measurements over time. For instance, if fatigue measurements are computed for a user after each workout over the course of an interval of time (such as a month, a year, etc.), the computed fatigue measurements can be displayed in a graph or chart that shows a change in fatigue measurement over time for the user. Such a display can beneficially enable a user to visualize athletic progress over time, thereby encouraging the user to continue with a particular exercise regimen or program. For example, the user can compare fatigue changes for the same workout. A lower fatigue measurement for a given workout over time demonstrates improved training performance.

The exercise program engine 300 modifies an exercise program based on a muscle fatigue measurement determined by the muscle fatigue engine 350. For instance, if a user is performing a workout consisting of sets of exercises, and one or more measures of fatigue of the user indicate that the user is becoming fatigued faster than normal, or is exceeding a threshold level of fatigue, the workout of the user can be modified to remove sets of exercises, to remove exercise reps, to reduce various weights or durations associated with the sets of exercises, and the like. Alternatively, if a user is performing the workout and one or more fatigue measurements indicate that the user is becoming fatigued slower than normal or is falling below a threshold level of fatigue, the workout of the user can be modified to add sets of exercises, to add exercise reps, to increase weights or durations associated with the sets of exercises, and the like. In some embodiments, trends in fatigue measurements associated with the user can result in the modification of the user's training plan, for instance by adding additional workouts if a user is generally becoming less fatigued over time, or by subtracting workouts if a user is generally becoming more fatigued over time.

It should be noted that fatigue measurements can be used to modify which muscle groups are being exercised during a workout. For instance, if a user is participating in a shoulders-focused workout, and one or more fatigue measurements indicate that the user's shoulder muscles are becoming fatigued, one or more future shoulder exercises in the workout can be changed to bicep exercises, leg exercises, or the like.

In some embodiments, one or more notifications or suggestions can be provided to the user based on fatigue measurements, where notifications can be provided to the user or an entity associated with the user (e.g., a coach, through a coaching tool or device). For instance, a rest interval between sets or exercises can be recommended in the event that one or more fatigue measurements indicate that the user is becoming tired more quickly than this user's historical average or a demographically similar average user. Alternatively, notifications or suggestions can be provided to the user in response to fatigue measurements indicating that the user is becoming tired slower than normal. For instance, if the user is running and one or more fatigue measurements indicate that the user is becoming less tired than normal, the user can be encouraged to run faster/pick up the pace.

In some embodiments, the muscle fatigue engine 350 accesses a pre-determined muscle fatigue measurement model (also referred to herein as a "model") stored in the model data store 370. The model defines one or more criteria for modifying the exercise program. For example, a set of criteria may be satisfied by the muscle fatigue engine 350 determining that a muscle fatigue measurement of an athlete exceeds a threshold deviation relative to athlete population norms, e.g., based on aggregate data retrieved from the athlete data store 310. Specifically, the model may indicate a target motion profile (e.g., indicative of proper form of an exercise to avoid injury) or muscle fatigue profile (e.g., indicating a decline in a muscle's ability to generate force), which may be customized based on the athlete's demographic or physiological data. If the athlete exceeds the threshold deviation, the muscle fatigue engine 350 may determine that the exercise program is currently too challenging (e.g., resulting in improper exercise form), not challenging enough (e.g., resulting in under-utilization of muscles) for the athlete, or not aligned with the user's goal. Thus, responsive to the muscle fatigue engine 350 determining that the set of criteria is satisfied by the muscle fatigue measurement, the exercise program engine 300 may adjust the difficulty of the exercise program to provide an appropriate level of challenge to the athlete.

The exercise program engine 300 may also modify an exercise program based on fatigue measurements, for example, to train imbalances. As such, an athlete can understand the accumulated fatigue placed on different muscle groups across multiple workouts and adjust if certain muscle groups are being biased over others. Imbalances can also be surfaced within a workout. For example, if a user is performing a bench press exercise, and is exerting more force with the user's left arm than the right arm, the left arm may become fatigued quicker, and this imbalance between measures of fatigue for the left arm and the right arm can be flagged to the user with a notification that the user's form was incorrect while performing the exercise.

The muscle fatigue engine 350 may determine the imbalance by examining the fatigue measurements determined across different muscle groups. If a fatigue measurement for one muscle group is greater than that of for other muscle groups by at least a threshold difference, the exercise program engine 300 determines that there is an imbalance. In response to this determination, the exercise program engine 300 may add or remove an exercise from the exercise program to address the imbalance. For instance, the exercise program engine 300 adds exercises to increase the force to be exerted by the "weaker" side of the body that currently fatigues more slowly.

Moreover, the muscle fatigue engine 350 may use fatigue measurements in combination with the user's strength in order to determine the user's performance for a particular exercise. For instance, during the performance of a bench press exercise, a user's right arm is associated with a greater measure of strength than the user's left arm, but the left arm is associated with a greater measure of fatigue than the right arm. In such an instance, a user can be determined to be strength imbalanced (e.g., stronger on the right side than the left side). Alternatively, if the user's right arm is associated with both greater measures of strength and fatigue, the user can be determined to be form imbalanced (e.g., using an improper form during the performance of the exercise). Such determinations can beneficially be communicated to the user. In the event that the user is form imbalanced, a notification to perform the exercise with proper form can be provided to the user. Likewise, if the user is strength imbalanced, additional exercises can be presented to the user to increase the strength in the under-strengthened muscle groups.

Further, the exercise program engine 300 may modify exercise programs based on other factors such as a measurement of strength, which may be determined based on historical muscle stress measurement and/or logs of how much weight has been involved or logs of other output the user has provided in relation to an activity. For instance, responsive to determining that the fatigue level is greater than a threshold level (e.g., indicative of chronic fatigue), the exercise program engine 300 removes exercises from the exercise program to alleviate the stress experienced by the athlete and mitigate injury risk from over training. In addition, the exercise program engine 300 may reduce the number or training stress of exercises during a period of time prior to an identified high stress event in the exercise program such as an athletic competition at which the athlete plans to participate. The exercise program engine 300 may provide a notification to an athlete describing a modification to an exercise program as well as relevant context. For example, the exercise program engine 300 notifies the athlete that chronic fatigue is detected and that the number of exercise sessions per week will be reduced accordingly, e.g., to mitigate injury risk. In some embodiments, the exercise program engine 300 presents an exercise program modification in a graphical user interface, e.g., highlighting an updated number of repetitions, sets, or weight for an exercise in a list, timeline, or calendar display of the athlete's exercise program. Additionally, the exercise program engine 300 may dynamically reformat or resize components of a graphical user interface based on modifications. For instance, a calendar display shows graphics (e.g., a window indicating a number of reps and weight for a particular type of exercise) corresponding to exercises for completion by the athlete on various days or times of the week. Responsive to a modification, the exercise program engine 300 removes existing graphics (e.g., with a cross mark or a faded color) or adds new graphics to the calendar (e.g., which may be emphasized in bold, with brighter colors, or with enlarged size).

Since the exercise program engine 300 can dynamically modify an exercise program and provide a notification of the modification while the athlete is performing the exercise program, the exercise feedback system 100 improves the athlete's training in real-time, instead of having the athlete or a coach review the athlete's performance after an exercise workout or session has been completed. Additionally, the exercise feedback system 100 may maintain accurate and continuous accumulation of physiological data even as the exercise program is modified. The exercise feedback system 100 may automatically update physiological data normalization or classifications for any number or type of modification of an exercise program, which allows athletes and coaches to receive reliable metrics and biofeedback while training.

In some embodiments, the exercise feedback system 100 uses the models to perform other functionality such as providing biofeedback by the biofeedback engine 380. The biofeedback engine 380 may generate or update various graphical user interfaces to present biofeedback via a client device 110. As an example, a model defines a set of criteria for determining a risk of injury. Responsive to the muscle fatigue engine 350 determining that the set of criteria is satisfied by an athlete's muscle fatigue measurement, the biofeedback engine 380 notifies the athlete of the risk of injury. In some embodiments, the biofeedback engine 380 communicates the risk of injury via a push notification presented by a client device 110 while an athlete is exercising, so that the athlete can promptly stop or adjust an exercise to avoid the injury. Further, an athletic garment worn by the athlete may also communicate the notification by providing haptic feedback, e.g., vibrating at a certain position on the athlete's body during an exercise to alert the athlete to reduce the weight being lifted or to correct improper form of an exercise. The biofeedback engine 380 may provide context with a notification of injury risk, for example, indicating a type of risk (e.g., straining a muscle or wearing out a joint), severity of the risk, or remedial action such as performing stretches, icing or heating a muscle, resting, or switching to a different type of exercise. In an example, the risk of injury may be determined based on an identified imbalance of muscle stress or a fatigue level of the athlete, and the biofeedback engine 380 provides context informing the athlete to increase training on the left or right side upper arm muscles (e.g., to address the identified imbalance) or reduce the amount of weights overall to recover from a high-risk fatigue level and avoid injury.

In addition to providing the notification of injury risk, the biofeedback engine 380 may also generate and provide other types of biofeedback for athletes based on the muscle fatigue measurements. The biofeedback indicates, for example, a metric of athletic performance such as a percentage value, a Boolean value (e.g., satisfactory or unsatisfactory), or any suitable type of value. In some embodiments, the biofeedback indicates a measure of progress of an athlete over a period of time and is generated based on context describing the corresponding exercise (e.g., using information from the athlete data store 310 or exercise program data store 320). The context may include a type of exercise, or a volumetric load based on a product of a number of repetitions and corresponding weights lifted by an athlete. The biofeedback may be generated based on heart rate data captured by sensors of an athletic garment or associated with a particular muscle, muscle group, repetition, or set. Based on normalized physiological data, the biofeedback engine 380 may generate biofeedback including a comparison between contributions of a set of muscles with that of a different set of muscles of the athlete while performing an exercise.

In some embodiments, the biofeedback engine 380 generates a graphical depiction of muscles of an athlete. In particular, the biceps and quads (among other types of muscles) may be overlaid on the arm and leg portions, respectively, of a human body graphic (e.g., resembling a silhouette, avatar, or the like) of the athlete. The biofeedback engine 380 may present muscle fatigue measurements, biofeedback, or other metrics of the muscles by dynamically updating a color or size of the graphic depiction of the corresponding muscle. For instance, as the muscle fatigue measurement increases, the graphic of the muscle becomes a brighter color, different color or increases in size to illustrate that the muscle is being fatigued for an exercise. Thus, the athlete can view a real-time progression of multiple muscles that increase or decrease in fatigue throughout stages of an exercise, e.g., the athlete utilizes the arm and leg muscles for different motions of an Olympic lift.

In some embodiments, some or all of the functionality of the exercise feedback system 100 may be performed by or implemented within a client device 110. For example, the client device 110 stores pre-determined muscle fatigue measurement models and uses a local muscle fatigue engine to determine whether a model's criteria for modifying an exercise program is satisfied. This can be advantageous because the client device 110 may not always have a network connection while an athlete is exercising (e.g., the athlete's gym does not have internet available). Thus, muscle fatigue measurements are determined and analyzed locally on the client device 110 without having to upload the physiological data to the exercise feedback system 100 for processing.

V. Example Process Flows

Figure 4:
FIG. 4 is a flowchart of a process for determining muscle fatigue measurements according to one embodiment.
Figure 4:
Figure 4:
Figure 4:
Figure 4:

FIG. 4 is a flowchart of a process 400 for determining muscle fatigue measurement according to one embodiment. In some embodiments, the process 400 is performed by the exercise feedback system 100—e.g., modules of the exercise feedback system 100 described with reference to FIG. 3—within the system environment in FIG. 1. The process 400 may include different or additional steps than those described in conjunction with FIG. 4 in some embodiments or perform steps in different orders than the order described in conjunction with FIG. 4.

In one embodiment, the data processing engine 330 receives 410 physiological data from an athletic garment worn by a user (athlete), where the physiological data describes muscle activation of muscles of the user while performing an exercise. The data processing engine 330 determines and removes 410 artifacts from the physiological data. For a particular muscle, the muscle fatigue engine 350 determines 430 a power spectrum of the conditioned data. The muscle fatigue engine 350 determines a spectrum ratio using the power spectrum. The muscle fatigue engine 350 determines a fatigue measurement using the spectrum ratio. For example, the muscle fatigue engine 350 may determine the spectrum ratio as the fatigue measurement or normalize the spectrum ratio relative to a distribution of spectrum ratio as the fatigue measurement. Alternatively, instead of determining a power spectrum and determining the ratio between frequency bands in the frequency domain, the muscle fatigue engine 350 filters the conditioned signal in the time domain using different frequency filters and calculates the ratio by using amplitudes of the output signal of the frequency filters. In some embodiments, the fatigue engine 350 determines and removes dynamic interference from the spectrum ratio to determine the fatigue measurement. The exercise feedback system presents 750 the muscle fatigue measurement to the user, e.g., by displaying biofeedback generated by the biofeedback engine 380 via a client device 110.

Figure 7:
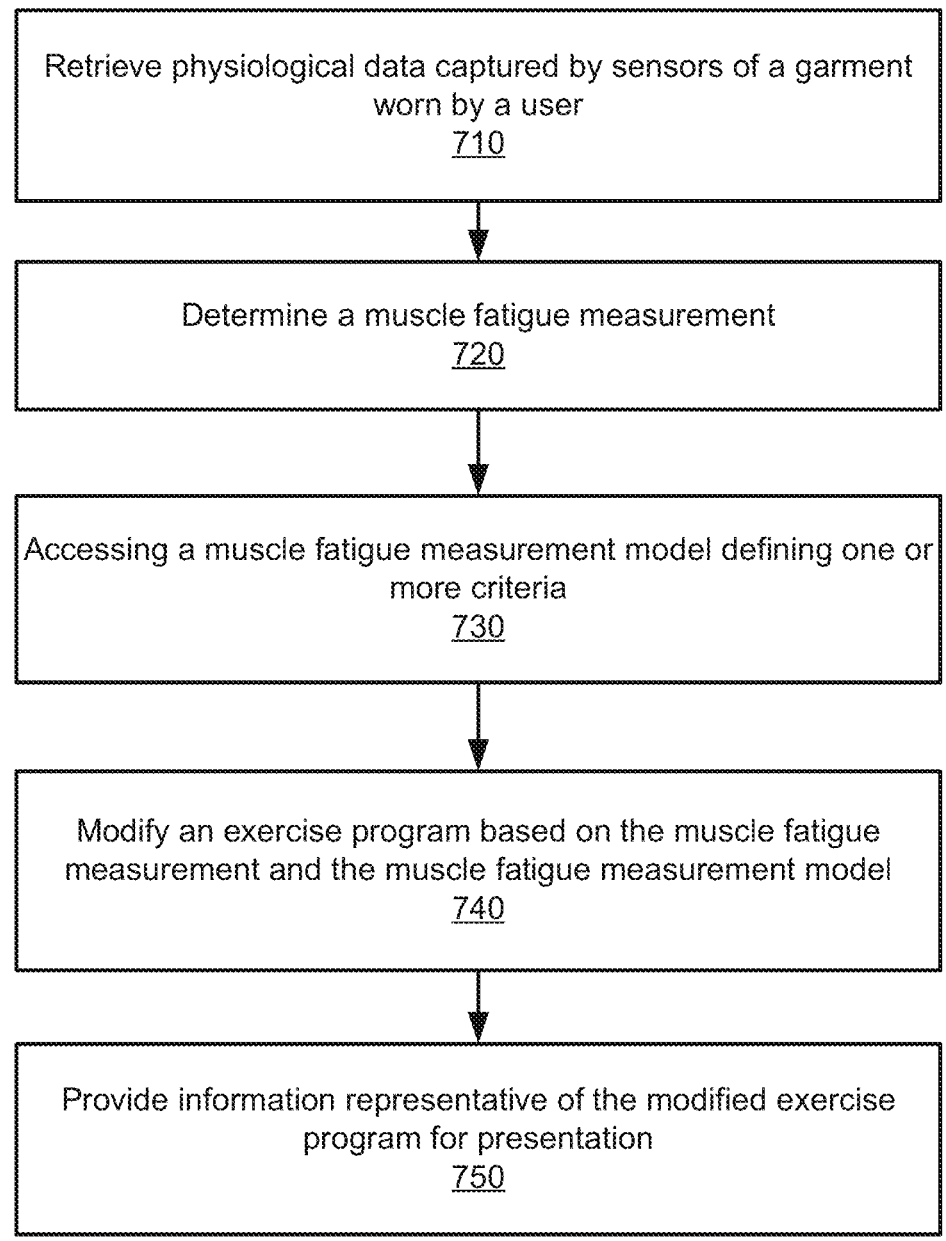
FIG. 7 is a flowchart of a process of managing an exercise program according to one embodiment.

Now referring to FIG. 7 that is a flowchart illustrating a process 700 of a process of managing an exercise program using a muscle fatigue measurement model according to one embodiment. In some embodiments, the process 700 is performed by the exercise feedback system 100—e.g., modules of the exercise feedback system 100 described with reference to FIG. 3—within the system environment in FIG. 1. The process 700 may include different or additional steps than those described in conjunction with FIG. 7 in some embodiments or perform steps in different orders than the order described in conjunction with FIG. 7.

In one embodiment, the data processing engine 330 retrieves 810 physiological data captured by sensors of an athletic garment worn by a user (athlete) while performing an exercise using a set of muscles for an exercise program presented to the user by a client device 110. The muscle fatigue engine 350 determines 720 a muscle fatigue measurement for the set of muscles that is representative of a fatigue degree of muscles over the course of the exercise (e.g., using the process 400 shown in FIG. 4). The muscle fatigue engine 350 accesses 730 a pre-determined muscle fatigue measurement model defining one or more criteria for modifying the exercise program. In response to at least one of the criteria being satisfied by the muscle fatigue measurement, the exercise program engine 300 modifies 740 the exercise program. The exercise program engine 300 presents 750 information representative of the modified exercise program by the client device 110. In other embodiments, the pre-determined muscle fatigue measurement model defines criteria for determining a risk of injury of the user. If the criteria being satisfied, the biofeedback engine 380 may provide a notification of the risk of injury to the user.

VI. Additional Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method comprising:
receiving physiological data from a set of electromyography (EMG) sensors of a garment worn by a user, the physiological data including EMG data describing muscle activation of a muscle of the user while performing an exercise, the set of sensors in contact with the muscle and generating the physiological data;
selecting a first portion and a second portion of the physiological data, the first portion corresponding to a first frequency band and the second portion corresponding to a second frequency band, the second frequency band higher than the first frequency band;
determining a muscle fatigue measurement of the muscle by determining a ratio between a power of the first frequency band and a power of the second frequency band; and
providing a recommendation to modify an exercise program of the user based on the determined muscle fatigue measurement for display to the user via a client device.

2. The method of claim 1, wherein selecting the first portion and the second portion of the physiological data comprises removing a baseline shift amount from the physiological data, the baseline shift amount corresponding to a third frequency band lower than a threshold frequency.

3. The method of claim 1, further comprising calculating a frequency spectrum of the physiological data over a time interval, wherein the first portion and the second portion of the physiological data correspond to the time interval.

4. The method of claim 1, wherein determining the muscle fatigue measurement further comprises determining a dynamic interference by:
generating an envelope of the physiological data,
selecting a first portion and a second portion of the envelope, the first portion corresponding to the first frequency band and the second portion corresponding to the second frequency band, and
determining a ratio between a power of the first frequency band of the envelope to a power of the second frequency band of the envelope.

5. The method of claim 4, further comprising removing the dynamic interference from the ratio between the power of the first frequency band of the physiological data and a power of the second frequency band of the physiological data.

6. The method of claim 1, further comprising heart rate variability data including a heart rate variability, further comprising:
determining a reference fatigue level based on the heart rate variability; and
determining a fatigue level of the user based on the reference fatigue level and the muscle fatigue measurement.

7. The method of claim 1, further comprising determining a time bound over which the muscle fatigue measurement is determined, wherein the physiological data is accumulated over the determined time bound.

8. The method of claim 1, further comprising normalizing the physiological data using one or more calibration parameters determined based on a muscle type of the muscle.

9. The method of claim 1, wherein determining the muscle fatigue measurement of the muscle for the exercise is further based on historical muscle fatigue measurements of exercises previously performed by the user, the muscle fatigue measurement indicating a pattern of performance of the muscle.

10. The method of claim 1, further comprising determining a time interval during which the physiological data is accumulated for determining the muscle fatigue measurement by classifying the physiological data.

11. The method of claim 10, wherein classifying the physiological data comprises:
determining active periods of time during which the user actively performed the exercise, the physiological data received during the active periods of time accumulated for the muscle fatigue measurement.

12. The method of claim 10, wherein classifying the physiological data comprises:
determining an inactive period of time during which the user did not actively perform the exercise, the physiological data received during the inactive period of time not accumulated for the muscle fatigue measurement.

13. The method of claim 1, further comprising:
determining a quality of physical contact between the set of EMG sensors and a portion of skin of the user during a period of time; and
responsive to determining that the quality of physical contact is less than a threshold quality, modifying the physiological data received during the period of time.

14. The method of claim 1, wherein the recommendation to modify the exercise program of the user comprises one or more of: modifying a rest interval between sets of the exercise, modifying a weight used in the exercise, modifying a pace of the exercise, modifying a duration of the exercise, modifying a number of repetitions in a set of the exercise, modifying a number of sets of the exercise, and adding another type of exercise to the exercise program.

15. The method of claim 1, further comprising:
determining a risk of injury to the muscle based on the muscle fatigue measurement; and
responsive to the determined risk of injury exceeding a threshold, providing a notification of the risk of injury for display to the user via the client device.

16. A computer program product comprising a non-transitory computer readable storage medium having instructions encoded thereon that, when executed by a processor, cause the processor to:
receive physiological data from a set of electromyography (EMG) sensors of a garment worn by a user, the physiological data including EMG data describing muscle activation of a muscle of the user while performing an exercise, the set of sensors in contact with the muscle and generating the physiological data;
select a first portion and a second portion of the physiological data, the first portion corresponding to a first frequency band and the second portion corresponding to a second frequency band, the second frequency band higher than the first frequency band;

determine a muscle fatigue measurement of the muscle by determining a ratio between a power of the first frequency band and a power of the second frequency band; and provide a recommendation to modify an exercise program of the user based on the determined muscle fatigue measurement for display to the user via a client device.

17. The computer program product of claim 16, wherein the computer instructions configured to cause the processor to select the first portion and the second portion of the physiological data comprises the computer instructions configured to cause the processor to remove a baseline shift amount from the physiological data, the baseline shift amount corresponding to a third frequency band lower than a threshold frequency.

18. The computer program product of claim 16, wherein the computer instructions are further configured to cause the processor to calculate a frequency spectrum of the physiological data over a time interval, wherein the first portion and the second portion of the physiological data correspond to the time interval.

19. The computer program product of claim 16, wherein the computer instructions configured to cause the processor to determine the muscle fatigue measurement further comprises computer instructions configured to cause the processor to determine a dynamic interference by:

generating phase-shifted physiological data by shifting the physiological data by 90 degrees, selecting a first portion and a second portion phase-shifted physiological data, the first portion corresponding to the first frequency band and the second portion corresponding to the second frequency band, and determining a ratio between a power of the first frequency band of the phase-shifted physiological data to a power of the second frequency band of the phase-shifted physiological data.

20. The computer program product of claim 19, wherein the computer instructions are further configured to cause the processor to remove the dynamic interference from the ratio between the power of the first frequency band of the physiological data and a power of the second frequency band of the physiological data.

21. A system comprising:

a garment worn by a user, the garment comprising a set of sensors; and a computing system comprising:
  a processor, and
  a memory storing instructions configured to cause the processor to perform:
    receiving physiological data from a set of electromyography (EMG) sensors of the garment worn by the user, the physiological data including EMG data describing muscle activation of a muscle of the user while performing an exercise, the set of sensors in contact with the muscle and generating the physiological data;
    selecting a first portion and a second portion of the physiological data, the first portion corresponding to a first frequency band and the second portion corresponding to a second frequency band, the second frequency band higher than the first frequency band;
    determining a muscle fatigue measurement of the muscle by determining a ratio between a power of the first frequency band and a power of the second frequency band; and
    providing a recommendation to modify an exercise program of the user based on the determined muscle fatigue measurement for display to the user via a client device.

* * * * *